United States Patent
Zhan et al.

(10) Patent No.: US 10,405,864 B2
(45) Date of Patent: Sep. 10, 2019

(54) LOADING UNIT WITH SHIPPING MEMBER FOR SURGICAL STAPLING DEVICE

(71) Applicant: Covidien LP, Mansfield, MA (US)

(72) Inventors: Hui Zhan, Shanghai (CN); Junyu Zhou, Minhang District (CN)

(73) Assignee: Covidien LP, Mansfield, MA (US)

( * ) Notice: Subject to any disclaimer, the term of this patent is extended or adjusted under 35 U.S.C. 154(b) by 326 days.

(21) Appl. No.: 15/319,976

(22) PCT Filed: Jul. 4, 2014

(86) PCT No.: PCT/CN2014/081621
§ 371 (c)(1),
(2) Date: Dec. 19, 2016

(87) PCT Pub. No.: WO2016/000247
PCT Pub. Date: Jan. 7, 2016

(65) Prior Publication Data
US 2017/0135696 A1    May 18, 2017

(51) Int. Cl.
*A61B 17/115* (2006.01)
*A61B 17/00* (2006.01)
*A61B 90/00* (2016.01)

(52) U.S. Cl.
CPC . *A61B 17/1155* (2013.01); *A61B 2017/00473* (2013.01); *A61B 2090/038* (2016.02); *A61B 2090/0801* (2016.02)

(58) Field of Classification Search
CPC . A61B 17/1155; A61B 17/105; A61B 17/072; A61B 50/30
USPC .............. 227/175.1, 176.1, 180.1, 19, 175.2
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

European Search Report dated Feb. 8, 2018, in EP Application No. 14896399.

(Continued)

*Primary Examiner* — Nathaniel C Chukwurah

(57) ABSTRACT

A loading unit (100) including a shipping member (200) is provided. The shipping member (200) is receivable on a distal end of the loading unit (100) in a first orientation to prevent movement of a pusher assembly (130) from a first to a second position and in a second orientation to effect separation of the loading unit (100) from a surgical stapling device (10).

19 Claims, 6 Drawing Sheets

(56) References Cited

U.S. PATENT DOCUMENTS

| | | |
|---|---|---|
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |

(56) References Cited

U.S. PATENT DOCUMENTS

| | | | |
|---|---|---|---|
| 6,491,201 B1 | 12/2002 | Whitman | |
| 6,494,877 B2 | 12/2002 | Odell et al. | |
| 6,503,259 B2 | 1/2003 | Huxel et al. | |
| 6,517,566 B1 | 2/2003 | Hovland et al. | |
| 6,520,398 B2 | 2/2003 | Nicolo | |
| 6,533,157 B1 | 3/2003 | Whitman | |
| 6,551,334 B2 | 4/2003 | Blatter et al. | |
| 6,578,751 B2 | 6/2003 | Hartwick | |
| 6,585,144 B2 | 7/2003 | Adams et al. | |
| 6,588,643 B2 | 7/2003 | Bolduc et al. | |
| 6,592,596 B1 | 7/2003 | Geitz | |
| 6,601,749 B2 | 8/2003 | Sullivan et al. | |
| 6,605,078 B2 | 8/2003 | Adams | |
| 6,605,098 B2 | 8/2003 | Nobis et al. | |
| 6,626,921 B2 | 9/2003 | Blatter et al. | |
| 6,629,630 B2 | 10/2003 | Adams | |
| 6,631,837 B1 | 10/2003 | Heck | |
| 6,632,227 B2 | 10/2003 | Adams | |
| 6,632,237 B2 | 10/2003 | Ben-David et al. | |
| 6,652,542 B2 | 11/2003 | Blatter et al. | |
| 6,659,327 B2 | 12/2003 | Heck et al. | |
| 6,676,671 B2 | 1/2004 | Robertson et al. | |
| 6,681,979 B2 | 1/2004 | Whitman | |
| 6,685,079 B2 | 2/2004 | Sharma et al. | |
| 6,695,198 B2 | 2/2004 | Adams et al. | |
| 6,695,199 B2 | 2/2004 | Whitman | |
| 6,698,643 B2 | 3/2004 | Whitman | |
| 6,716,222 B2 | 4/2004 | McAlister et al. | |
| 6,716,233 B1 | 4/2004 | Whitman | |
| 6,726,697 B2 | 4/2004 | Nicholas et al. | |
| 6,742,692 B2 | 6/2004 | Hartwick | |
| 6,743,244 B2 | 6/2004 | Blatter et al. | |
| 6,763,993 B2 | 7/2004 | Bolduc et al. | |
| 6,769,590 B2 | 8/2004 | Vresh et al. | |
| 6,769,594 B2 | 8/2004 | Orban, III | |
| 6,820,791 B2 | 11/2004 | Adams | |
| 6,821,282 B2 | 11/2004 | Perry et al. | |
| 6,827,246 B2 | 12/2004 | Sullivan et al. | |
| 6,840,423 B2 | 1/2005 | Adams et al. | |
| 6,843,403 B2 | 1/2005 | Whitman | |
| 6,846,308 B2 | 1/2005 | Whitman et al. | |
| 6,852,122 B2 | 2/2005 | Rush | |
| 6,866,178 B2 * | 3/2005 | Adams | A61B 17/072 227/156 |
| 6,872,214 B2 | 3/2005 | Sonnenschein et al. | |
| 6,874,669 B2 | 4/2005 | Adams et al. | |
| 6,884,250 B2 | 4/2005 | Monassevitch et al. | |
| 6,905,504 B1 | 6/2005 | Vargas | |
| 6,938,814 B2 | 9/2005 | Sharma et al. | |
| 6,942,675 B1 | 9/2005 | Vargas | |
| 6,945,444 B2 | 9/2005 | Gresham et al. | |
| 6,953,138 B1 | 10/2005 | Dworak et al. | |
| 6,957,758 B2 | 10/2005 | Aranyi | |
| 6,959,851 B2 | 11/2005 | Heinrich | |
| 6,978,922 B2 | 12/2005 | Bilotti et al. | |
| 6,981,941 B2 | 1/2006 | Whitman et al. | |
| 6,981,979 B2 | 1/2006 | Nicolo | |
| 7,032,798 B2 | 4/2006 | Whitman et al. | |
| 7,059,331 B2 | 6/2006 | Adams et al. | |
| 7,059,510 B2 | 6/2006 | Orban, III | |
| 7,077,856 B2 | 7/2006 | Whitman | |
| 7,080,769 B2 | 7/2006 | Vresh et al. | |
| 7,086,267 B2 | 8/2006 | Dworak et al. | |
| 7,114,642 B2 | 10/2006 | Whitman | |
| 7,118,528 B1 | 10/2006 | Piskun | |
| 7,122,044 B2 | 10/2006 | Bolduc et al. | |
| 7,128,748 B2 | 10/2006 | Mooradian et al. | |
| 7,141,055 B2 | 11/2006 | Abrams et al. | |
| 7,168,604 B2 | 1/2007 | Milliman et al. | |
| 7,179,267 B2 | 2/2007 | Nolan et al. | |
| 7,182,239 B1 | 2/2007 | Myers | |
| 7,195,142 B2 | 3/2007 | Orban, III | |
| 7,207,168 B2 | 4/2007 | Doepker et al. | |
| 7,220,237 B2 | 5/2007 | Gannoe et al. | |
| 7,234,624 B2 | 6/2007 | Gresham et al. | |
| 7,235,089 B1 | 6/2007 | McGuckin, Jr. | |
| RE39,841 E | 9/2007 | Bilotti et al. | |
| 7,285,125 B2 | 10/2007 | Viola | |
| 7,303,106 B2 | 12/2007 | Milliman et al. | |
| 7,303,107 B2 | 12/2007 | Milliman et al. | |
| 7,309,341 B2 | 12/2007 | Ortiz et al. | |
| 7,322,994 B2 | 1/2008 | Nicholas et al. | |
| 7,325,713 B2 | 2/2008 | Aranyi | |
| 7,334,718 B2 | 2/2008 | McAlister et al. | |
| 7,335,212 B2 | 2/2008 | Edoga et al. | |
| 7,364,060 B2 | 4/2008 | Milliman | |
| 7,398,908 B2 | 7/2008 | Holsten et al. | |
| 7,399,305 B2 | 7/2008 | Csiky et al. | |
| 7,401,721 B2 | 7/2008 | Holsten et al. | |
| 7,401,722 B2 | 7/2008 | Hur | |
| 7,407,075 B2 | 8/2008 | Holsten et al. | |
| 7,410,086 B2 | 8/2008 | Ortiz et al. | |
| 7,422,137 B2 | 9/2008 | Manzo | |
| 7,422,138 B2 | 9/2008 | Bilotti et al. | |
| 7,431,191 B2 | 10/2008 | Milliman | |
| 7,438,718 B2 | 10/2008 | Milliman et al. | |
| 7,455,676 B2 | 11/2008 | Holsten et al. | |
| 7,455,682 B2 | 11/2008 | Viola | |
| 7,481,347 B2 | 1/2009 | Roy | |
| 7,494,038 B2 | 2/2009 | Milliman | |
| 7,506,791 B2 | 3/2009 | Omaits et al. | |
| 7,516,877 B2 | 4/2009 | Aranyi | |
| 7,527,185 B2 | 5/2009 | Harari et al. | |
| 7,537,602 B2 | 5/2009 | Whitman | |
| 7,540,839 B2 | 6/2009 | Butler et al. | |
| 7,546,939 B2 | 6/2009 | Adams et al. | |
| 7,546,940 B2 | 6/2009 | Milliman et al. | |
| 7,547,312 B2 | 6/2009 | Bauman et al. | |
| 7,556,186 B2 | 7/2009 | Milliman | |
| 7,559,451 B2 | 7/2009 | Sharma et al. | |
| 7,585,306 B2 | 9/2009 | Abbott et al. | |
| 7,588,174 B2 | 9/2009 | Holsten et al. | |
| 7,600,663 B2 | 10/2009 | Green | |
| 7,611,038 B2 | 11/2009 | Racenet et al. | |
| 7,635,385 B2 | 12/2009 | Milliman et al. | |
| 7,669,747 B2 | 3/2010 | Weisenburgh, II et al. | |
| 7,686,201 B2 | 3/2010 | Csiky | |
| 7,694,864 B2 | 4/2010 | Okada et al. | |
| 7,699,204 B2 | 4/2010 | Viola | |
| 7,708,181 B2 | 5/2010 | Cole et al. | |
| 7,717,313 B2 | 5/2010 | Criscuolo et al. | |
| 7,721,932 B2 | 5/2010 | Cole et al. | |
| 7,726,539 B2 | 6/2010 | Holsten et al. | |
| 7,743,958 B2 | 6/2010 | Orban, III | |
| 7,744,627 B2 | 6/2010 | Orban, III et al. | |
| 7,770,776 B2 | 8/2010 | Chen et al. | |
| 7,771,440 B2 | 8/2010 | Ortiz et al. | |
| 7,776,060 B2 | 8/2010 | Mooradian et al. | |
| 7,793,813 B2 | 9/2010 | Bettuchi | |
| 7,802,712 B2 | 9/2010 | Milliman et al. | |
| 7,823,592 B2 | 11/2010 | Bettuchi et al. | |
| 7,837,079 B2 | 11/2010 | Holsten et al. | |
| 7,837,080 B2 | 11/2010 | Schwemberger | |
| 7,837,081 B2 | 11/2010 | Holsten et al. | |
| 7,845,536 B2 | 12/2010 | Viola et al. | |
| 7,845,538 B2 | 12/2010 | Whitman | |
| 7,857,187 B2 | 12/2010 | Milliman | |
| 7,886,951 B2 | 2/2011 | Hessler | |
| 7,896,215 B2 | 3/2011 | Adams et al. | |
| 7,900,806 B2 | 3/2011 | Chen et al. | |
| 7,909,039 B2 | 3/2011 | Hur | |
| 7,909,219 B2 | 3/2011 | Cole et al. | |
| 7,909,222 B2 | 3/2011 | Cole et al. | |
| 7,909,223 B2 | 3/2011 | Cole et al. | |
| 7,913,892 B2 | 3/2011 | Cole et al. | |
| 7,918,377 B2 | 4/2011 | Measamer et al. | |
| 7,922,062 B2 | 4/2011 | Cole et al. | |
| 7,922,743 B2 | 4/2011 | Heinrich et al. | |
| 7,931,183 B2 | 4/2011 | Orban, III | |
| 7,938,307 B2 | 5/2011 | Bettuchi | |
| 7,942,302 B2 | 5/2011 | Roby et al. | |
| 7,951,166 B2 | 5/2011 | Orban, III et al. | |
| 7,959,050 B2 | 6/2011 | Smith et al. | |
| 7,967,181 B2 | 6/2011 | Viola et al. | |

(56) References Cited

U.S. PATENT DOCUMENTS

| | | |
|---|---|---|
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0119901 A1* | 5/2007 | Ehrenfels ......... A61B 17/07207 227/176.1 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0006100 A1 | 1/2011 | Milliam |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145714 A1* | 6/2012 | Farascioni ............ A61B 17/072 220/260 |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |

(56) References Cited

U.S. PATENT DOCUMENTS

| | | |
|---|---|---|
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |

FOREIGN PATENT DOCUMENTS

| | | |
|---|---|---|
| CN | 2868208 Y | 2/2007 |
| CN | 101843509 A | 9/2010 |
| CN | 201683945 U | 12/2010 |
| CN | 102048568 A | 5/2011 |
| CN | 102843977 A | 12/2012 |
| CN | 103800043 A | 5/2014 |
| CN | 104758019 A | 7/2015 |
| CN | 106061410 A | 10/2016 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2499987 A2 | 9/2012 |
| EP | 2524656 A2 | 11/2012 |
| EP | 2730237 A1 | 5/2014 |
| EP | 2891462 A1 | 7/2015 |
| EP | 3122261 A1 | 2/2017 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013511344 A | 4/2013 |
| JP | 2013-138860 A | 7/2013 |
| JP | 2014094282 A | 5/2014 |
| JP | 2014094283 A | 5/2014 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 2001/054594 A1 | 8/2001 |
| WO | 2008/107918 A1 | 9/2008 |

OTHER PUBLICATIONS

Japanese Office Action dated Apr. 9, 2018, in Japanese Appln. No. 2017519752.

International Search Report for date of completion is Mar. 19, 2015 (4 pages).

Chinese Office Action dated Aug. 28, 2018, issued in CN Appln. No. 201480080806.

* cited by examiner

LOADING UNIT WITH SHIPPING MEMBER FOR SURGICAL STAPLING DEVICE

CROSS-REFERENCE TO RELATED APPLICATIONS

This application is a National Stage Application of PCT/CN14/081621under 35USC § 371 (a), the disclosure of the above-identified application is hereby incorporated by reference in its entirety.

TECHNICAL FIELD

The present disclosure relates to surgical stapling devices including a replaceable loading unit. More particularly, to a shipping member which prevents firing of the loading unit prior to detachment of the shipping member from the loading unit and facilitates detachment of the loading unit from the surgical stapling device.

BACKGROUND

Circular stapling apparatus are commonly used to join tubular tissue sections by circular anastomosis. Typically, circular stapling apparatus include a loading unit for applying a circular array of staples to the tissue. The loading units are typically replaceable after firing to permit reuse of the circular stapling apparatus. During shipping and attachment of the loading units to the circular stapling apparatus, pusher and knife assemblies within the loading unit may become misaligned, preventing proper attachment of the loading unit to the circular stapling apparatus. Further, once fired, the loading unit does not include any mechanism for preventing subsequent firing of the empty loading unit and/or that facilitates detaching the loading unit from the circular stapling apparatus. To ensure proper attachment of the loading unit to the surgical stapling apparatus, to prevent firing of an empty loading unit, and to facilitate separation of the loading unit from the circular stapling apparatus, it would be desirable to provide a shipping member which maintains the loading unit in an operable condition and is reattached to the loading unit after firing.

SUMMARY

A loading unit for a circular stapling apparatus is provided. The loading unit includes a housing defining a pair of first openings and a pair of second openings, a pusher assembly operably received within the housing and movable from a first position to a second position within the housing, a staple cartridge disposed on a distal end of the housing and including a plurality of staples, and a shipping member operably received on a distal end of the housing to prevent movement of the pusher assembly from the first to the second position. The first openings of the housing may be larger than the second openings. The shipping member may be receivable on the housing in a first orientation and a second orientation. In the first orientation the shipping member may be removably secured to the housing and in the second orientation the shipping member may be fixedly secured to the housing.

In one embodiment, the shipping member includes a base portion, a pair of legs extending from the base portion, and a locking feature disposed on a free end of each of the pair of legs. The locking features may be removably securable within the pair of first openings and fixedly securable within the pair of second opening. The base portion of the shipping member may include an inner surface configured to be disposed adjacent the staple cartridge. The inner surface of the base portion may be configured to maintain the plurality of staples within the staple cartridge. The shipping member may further include a retaining portion extending proximally from the base portion. The retaining portion may be configured to engage the pusher assembly. The retaining portion may include at least one extension. The at least one extension may include a pair of extensions. Each locking feature may include a pair of flanges and each of the pair of flanges may be configured to flex inwardly to facilitate entry of the flanges into one of the second openings. Each flange may include a projection extending radially outward therefrom. Each leg of the pair of legs may include a tab to facilitate operable engagement by a user.

A surgical stapling device is also provided. The surgical stapling device includes a body portion, a loading unit removably secured to the body portion, and a shipping member operably received on a distal end of the loading unit. The shipping member may be receivable on the loading unit in a first orientation and a second orientation. In the second orientation the shipping member may effect separation of the loading unit from the body portion. The loading unit may include a pusher assembly and the body portion may include a drive assembly, the pusher assembly may be removably secured to the drive assembly. Engagement of the shipping member with the pusher assembly may disengage the pusher assembly from the drive assembly. The shipping member may include at least one retaining portion for engaging the pusher assembly. The loading unit may include a housing and the at least one retaining feature may include projection. The projection may engage the housing when the shipping member is in the second orientation to fixedly secure the shipping member to the housing.

Also provided is a method of stapling tissue. The method includes attaching a loading unit to a surgical stapling device, the loading unit including a shipping member secured thereto in a first orientation, removing the shipping member from the loading unit, performing a stapling procedure with the surgical stapling device and the loading unit, and securing the shipping member to the loading unit in a second orientation. The method may further include separating the loading unit from the surgical stapling device subsequent to securing the shipping member to the loading unit in the second orientation. Securing the shipping member to the loading unit may include engaging a retaining portion of the shipping member with a pusher assembly of the loading unit. Engaging the retaining portion of the shipping member with the pusher assembly may include disengaging the pusher assembly from a drive assembly of the surgical stapling device.

BRIEF DESCRIPTION OF THE DRAWINGS

The accompanying drawings, which are incorporated in and constitute a part of this specification, illustrate an embodiment of the disclosure and, together with a general description of the disclosure given above, and the detailed description of the embodiment given below, serve to explain the principles of the disclosure, wherein.

DETAILED DESCRIPTION

Figure 1:
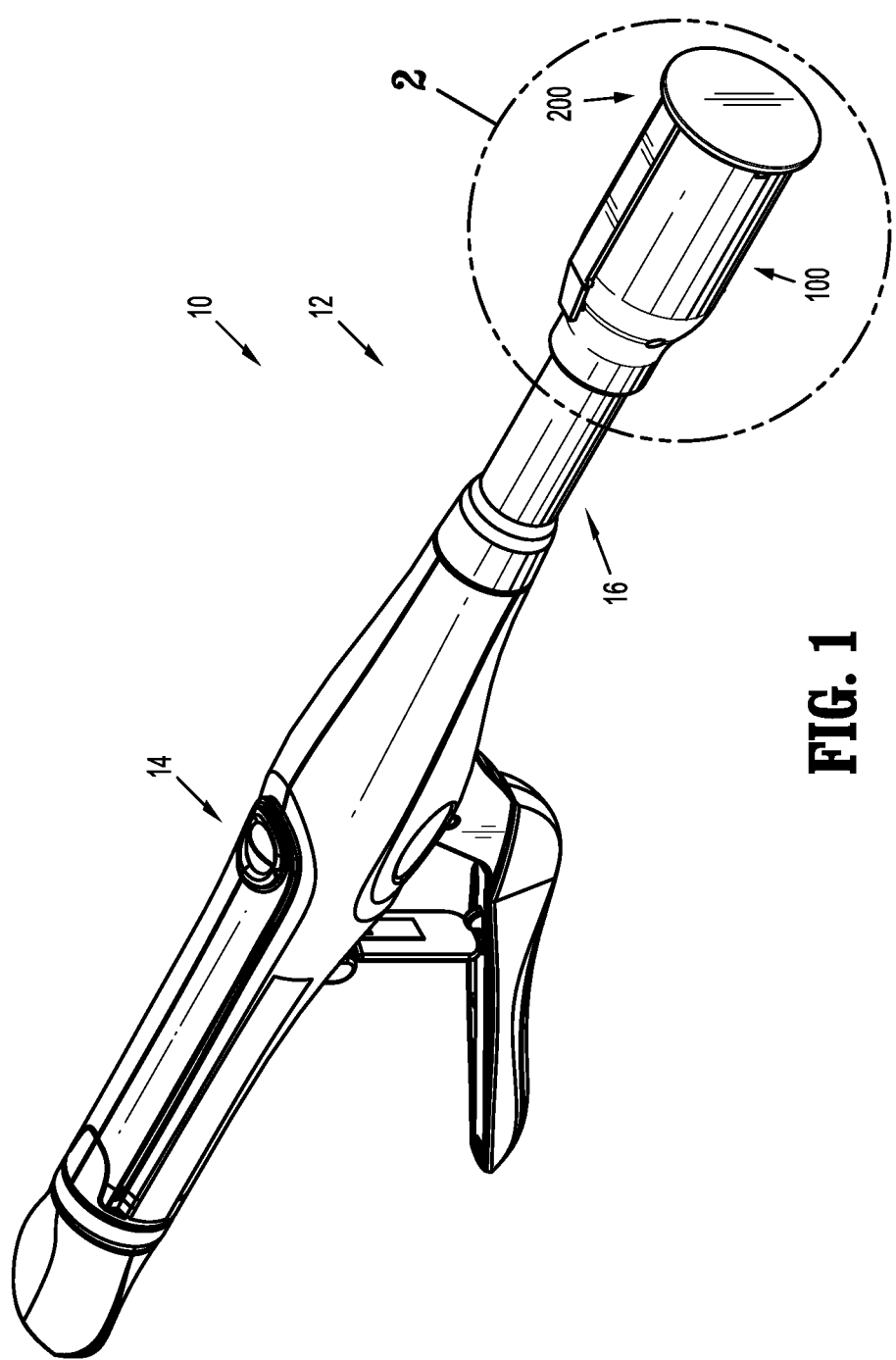
FIG. 1 is a perspective side view of a surgical stapling device including a loading unit, according to an embodiment of the present disclosure, and a shipping member, according to an embodiment of the present disclosure, secured to the loading unit.

Embodiments of the presently disclosed loading unit and shipping member will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

With reference to FIG. 1, a surgical stapling device 10 includes a replaceable loading unit, according to an embodiment of the present disclosure, shown generally as loading unit 100, and a shipping member, according to an embodiment of the present disclosure, shown generally as shipping cap 200. Loading unit 100 is shown operably connected to an elongate body 16 of an actuation unit 12 of surgical stapling device 10. For a detailed description of an exemplary actuation unit 12, please refer to commonly owned U.S. Pat. No. 8,590,763 ("the '763 patent"), the content of which is incorporated by reference herein in its entirety.

Figure 2:
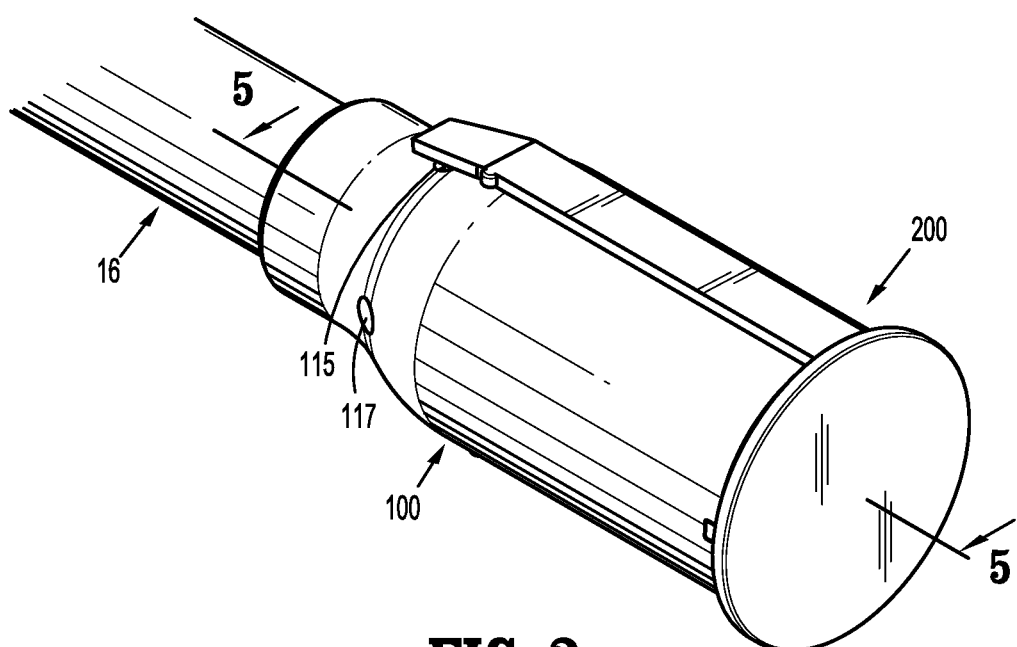
FIG. 2 is a perspective view of the identified area shown in FIG. 1.

With reference to FIGS. 1 and 2, shipping cap 200 is selectively received on a distal end of loading unit 100 and operates to maintain staples "S" (FIG. 4) within a staple cartridge 120 (FIG. 4) of loading unit 100 and to prevent premature advancement of pusher member 130 (FIG. 4) prior to and during attachment of loading unit 100 to elongate body 16 of actuation unit 12. In addition, shipping cap 200 operates to prevent re-firing of loading unit 100 once shipping cap 200 has been reattached to loading unit 100. In addition, reattaching shipping cap 200 to loading unit 100 after firing of loading unit 100 facilitates separation of loading unit 100 from elongate body 16 of actuation unit 12, as will be described in further detail below.

Although loading unit 100 will be described with reference to shipping cap 200, and shipping cap 200 will be described with reference to loading unit 100, it is envisioned that the aspects of the present disclosure may be modified for use with loading units and shipping caps having different configurations. Loading unit 100 will only be described to the extent necessary to fully disclose the aspects of the present disclosure. For a more detailed description of an exemplary loading unit, please refer to the '763 patent, the content of which was previously incorporated herein by reference.

With reference to FIGS. 2-5, loading unit 100 includes a housing 110, a staple cartridge 120 secured to a distal end of housing 110, and a pusher member 130 (FIG. 3) operably received within housing 110. Housing 110 of loading unit 100 includes an outer cylindrical portion 112 and an inner cylindrical portion 114. A plurality of ribs (not shown) interconnects outer and inner cylindrical portions 112, 114. Outer cylindrical portion 112 and inner cylindrical portion 114 of housing 110 are coaxial and define a cavity 113 configured to slidably receive pusher member 130. A proximal end of housing 110 is configured for selective connection to elongate body 16 of actuation unit 12 or an adapter assembly (not shown) that is connected to actuation unit 12. For example, housing 110 of loading unit 100 may connect to elongate body 16 or the adapter assembly with a bayonet coupling or in any suitable manner.

Figure 3:
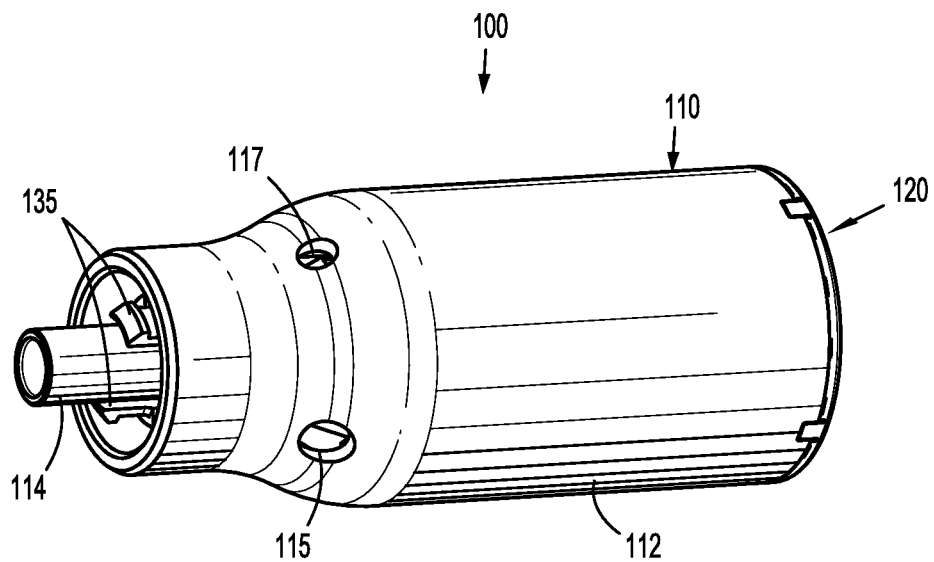
FIG. 3 is a perspective side view of the loading unit shown in FIGS. 1 and 2, separated from the surgical stapling device and with the shipping member removed.

With particular reference to FIGS. 2 and 3, outer cylindrical portion 112 of housing 110 defines large openings 115 which are longitudinally spaced from the distal end of loading unit 100 and extend through the outer cylindrical portion 112. Large openings 115 are positioned diametrically opposite one another (FIG. 7) in outer cylindrical portion 112 and are configured to receive a locking feature 226 (FIG. 8) of shipping cap 200. Outer cylindrical portion 112 of housing 110 also defines small openings 117 which are longitudinally spaced from the distal end of loading unit 100 and extend through outer cylindrical portion 112. The small openings 117 are circumferentially spaced from large openings 115 and are positioned diametrically opposite one another (FIG. 9) and extend through outer cylindrical portion 112. The small openings 117 are configured to securely receive locking feature 226 (FIG. 8) of shipping cap 200.

Figure 4:
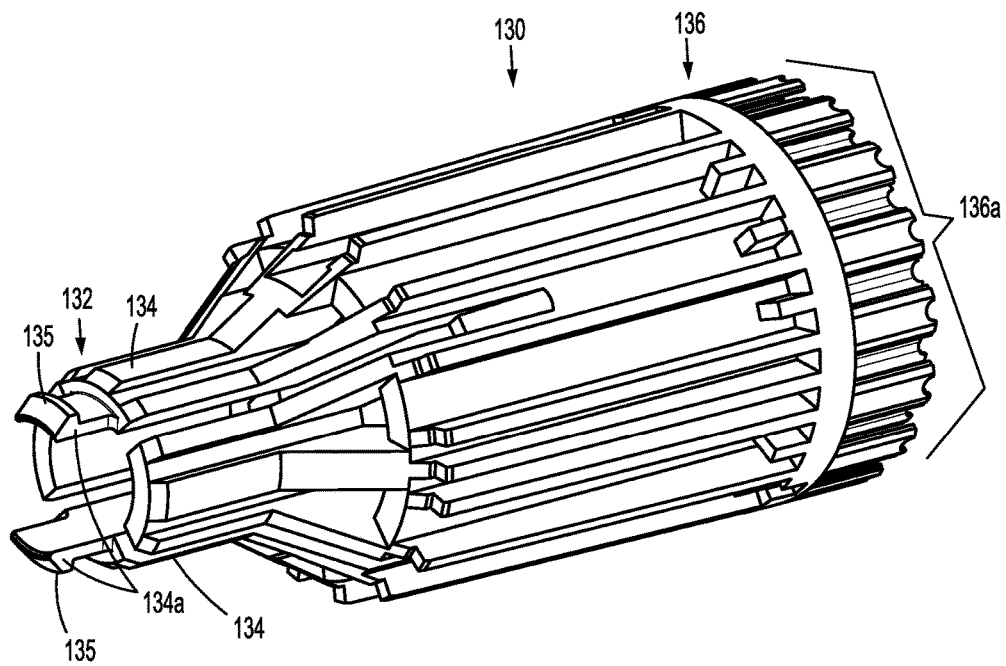
FIG. 4 is a perspective view of a pusher member of the loading unit shown in FIGS. 1-3.
Figure 5:
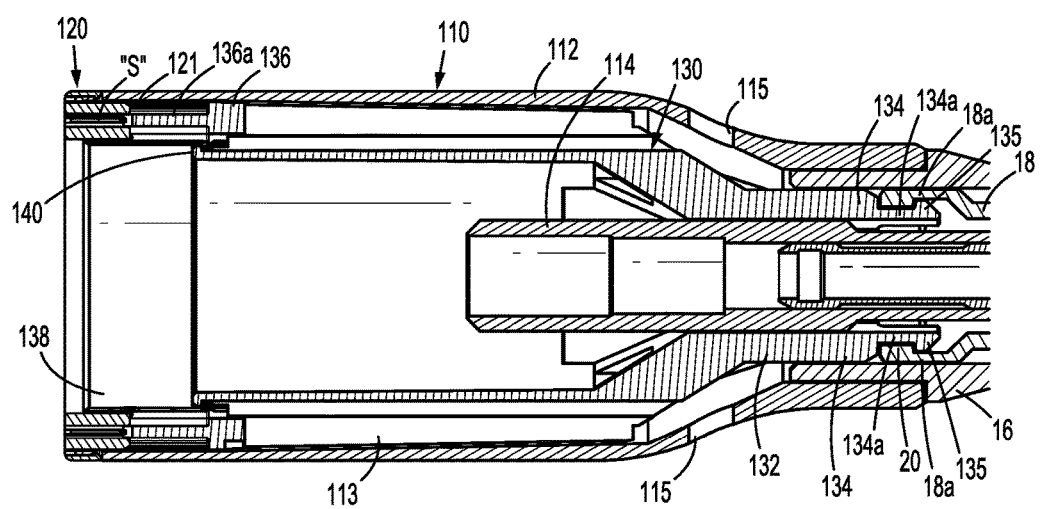
FIG. 5 is a cross-sectional side view taken along line 5-5 shown in FIG. 2.

With reference to FIGS. 4 and 5, staple cartridge 120 of loading unit 100 is secured to a distal end of housing 110 and includes a plurality of staple pockets 121 (FIG. 5). Each staple pocket 121 is configured to receive and retain a plurality of staples "S".

The pusher member 130 of loading unit 100 includes a proximal end 132 configured to releasably couple to a drive mechanism 18 (FIG. 1) of the actuation unit 12. Specifically, proximal end 132 of pusher member 130 includes a pair of arms 134 including a tab 135 formed on a proximal end 134a of each arm 134. Tabs 135 are configured for releasable engagement with a notched distal end 18a of drive member 18 of actuation unit 12. As will be discussed in further detail below, proximal ends 134a of arms 134 are configured to flex radially inward to facilitate connection of pusher member 130 to drive member 18 and to facilitate separation of pusher member 130 from drive member 18. A distal end 136 of pusher member 130 includes a plurality of staple pushers 136a which are received within staple pockets 121 of staple cartridge 120 in a position to engage the staples "S". Advancement of pusher member 130 within staple cartridge 120 causes ejection of staples "S" from staple cartridge 120. A circular knife 138 is secured to a shelf 140 (FIG. 5) formed within pusher member 130 adjacent staple pushers 136a on distal end 136 of pusher member 130. Circular knife 138 is configured to move distally with pusher member 130 within the staple cartridge 120 to cut tissue (not shown) within the stapled tissue.

Figure 6:
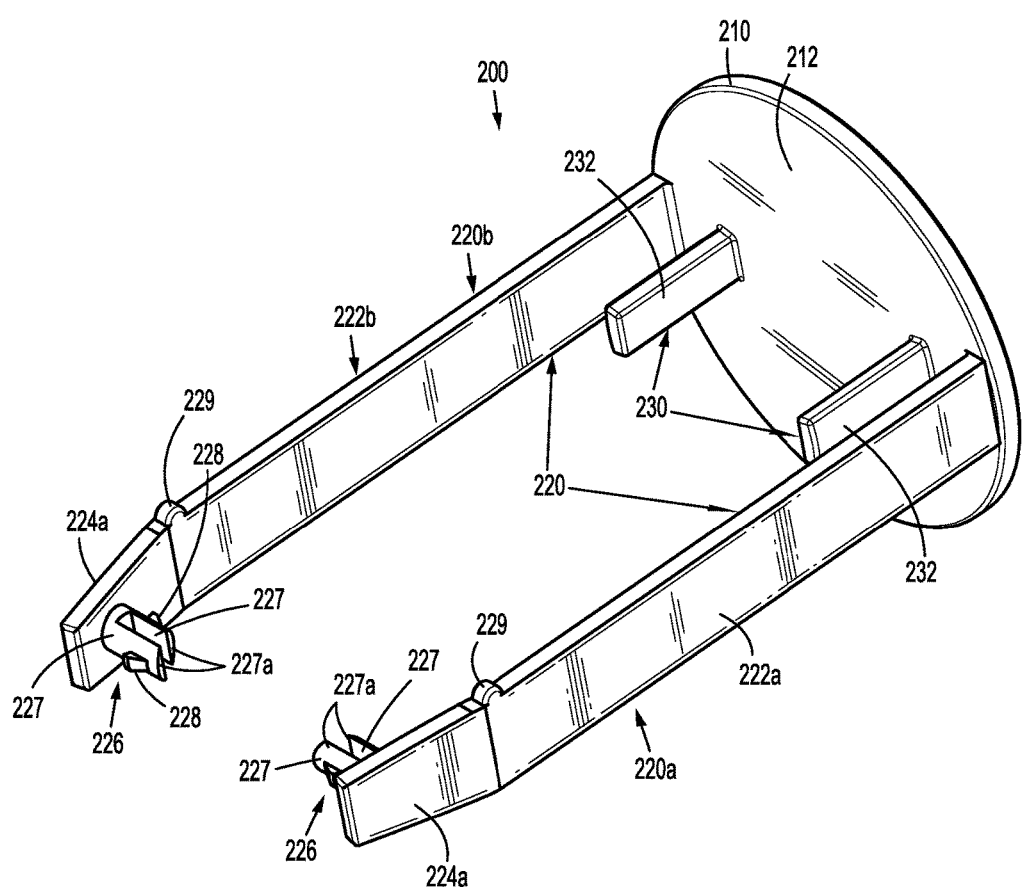
FIG. 6 is a perspective view of the shipping member shown in FIGS. 1 and 2.

With particular reference now to FIG. 6, shipping cap 200 is configured to be selectively received on a distal end of loading unit 100 (FIG. 2). Shipping cap 200 includes a base portion 210, attachment portion 220, and retainer portion 230. Although shown as being of one-piece construction, i.e., integrally or monolithically formed, it is envisioned that base portion 210, attachment portion 220, and/or retaining portion 230 may be independently formed and secured together with adhesive, welding, or in any other suitable manner.

Base portion 210 of shipping cap 200 includes a substantially flat or planar body having a circular shape. Although shown having a circular shape, it is envisioned that base portion 210 may include any shape corresponding to the cross-sectional shape of loading unit 100 (FIG. 1). It is further envisioned that base portion 210 may be conical in shape or otherwise configured to facilitate insertion and positioning of loading unit 100 within tissue (not shown) of a patient (not shown).

A proximal facing surface 212 of base portion 210 of shipping cap 200 is configured to abut a distal face of staple cartridge 120 of loading unit 100 when shipping cap 100 is attached to the distal end of loading unit 100 to retain staples "S" within the staple cartridge 120. Staple retaining surface 212 operates to retain staples "S" (FIG. 5) within staple pockets 121 (FIG. 5) of staple cartridge 120 (FIG. 5) during shipment and attachment of loading unit 100 to elongate body 16 of actuation unit 12 (FIG. 1). Although shown as being circular so as to correspond with the cross-sectional shape of staple cartridge 120 of loading unit 100, it is envisioned that staple retaining surface 212 of base portion 210 may be modified to correspond with staple cartridges having other cross-sectional configurations or may have a configuration other than that of the staple cartridge.

Attachment portion 220 of shipping cap 200 includes a pair of legs 220a, 220b extending proximally from base portion 210. Each leg 220a, 220b includes a first section 222a, 222b that extends perpendicularly from base portion 210 and a second section 224a, 224b that extends at an angle relative to respective first sections 222a, 222b. As seen in FIG. 2, first and second sections 222a, 222b, 224a, 224b of respective legs 220a, 220b conform to the shape of outer cylindrical portion 112 of housing 110 of loading unit 100.

A locking feature 226 extends radially inwardly from each of second sections 224a, 224b of legs 220a, 220b of attachment portion 220. Each locking feature 226 includes a plurality of inwardly deformable flanges 227. Although shown including a pair of flanges 227, it is envisioned that locking feature 226 may include more then two flanges 227. Each flange 227 is configured to flex towards the other flange 227 of the pair of flanges 227. As will be described in further detail below, a free end 227a of each flange 227 is configured to engage an outer surface of an arm 134 of pusher member 130 of loading unit 100 to facilitate the release of pusher member 130 from drive member 18 (FIG. 5) of actuation unit 12 (FIG. 1), as will be described in further detail below. A projection 228 extends outwardly from each flange 227. As will also be described in further detail below, projections 228 on flanges 227 are configured to engage outer cylindrical portion 112 of housing 110 of loading unit 100. Each leg 220a, 220b includes a tab 229 or other feature configured for engagement by a user to facilitate flexion of legs 220a, 220b away from outer cylindrical portion 112 of housing 110 of loading unit 100 to permit separation of shipping cap 200 from loading unit 100.

Retainer portion 230 of shipping cap 200 extends perpendicularly from a plane defined by the base portion 210. As shown, retainer portion 230 includes two extensions 232. Retainer portion 230 may instead include only a single extension or more than two extensions. In an alternative embodiment, retainer portion 230 includes an annular extension. Extensions 232 are configured to be received within distal end 136 of pusher member 130 of loading unit 100 and engage shelf 140 of pusher member 130 when shipping cap 200 is attached to loading unit 100. Engagement of extensions 232 of retaining portion 230 of shipping cap 200 with shelf 140 of pusher member 130 of loading unit 100 prevents advancement of pusher member 130 while shipping cap 200 is attached to loading unit 100.

Figure 7:
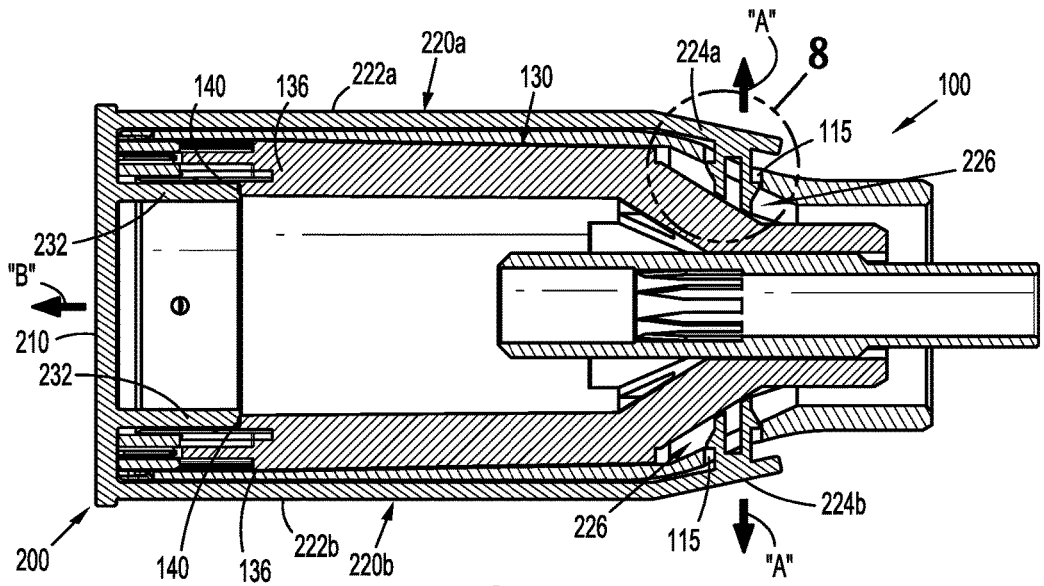
FIG. 7 is a cross-sectional side view of the loading unit shown in FIGS. 1-3, including the shipping member shown in FIG. 6 attached to the loading unit in a first orientation.
Figure 8:
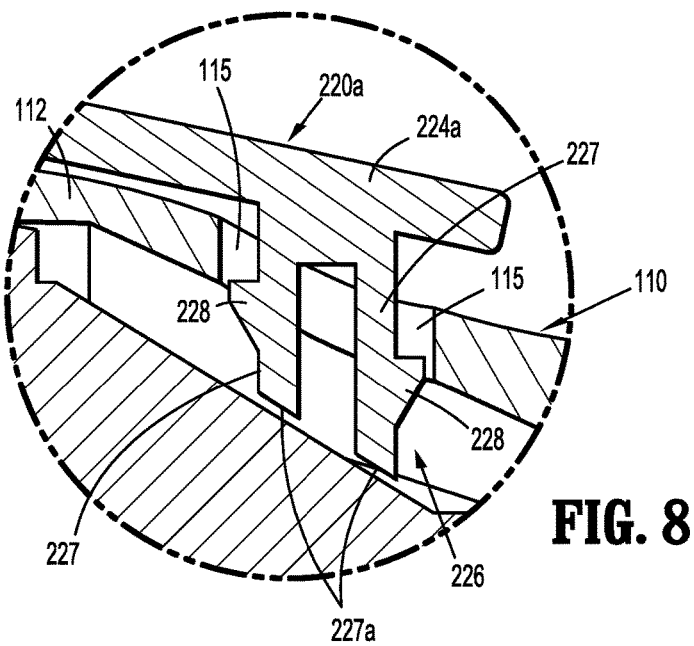
FIG. 8 is an enlarged view of the indicated area shown in FIG. 7.
Figure 9:
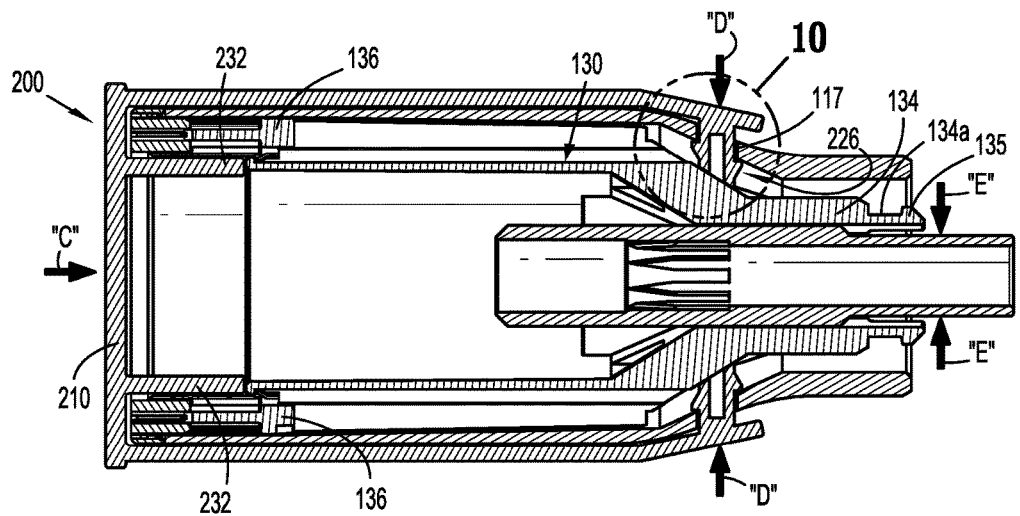
FIG. 9 is a cross-sectional side view of the loading unit shown in FIGS. 1-3, including the shipping member shown in FIG. 6 attached to the loading unit in a second orientation.

With reference now to FIGS. 7 and 8, shipping cap 200 is shown attached to loading unit 100. When shipping cap 200 is attached to loading unit 100 in a first or pre-fired orientation, flanges 227 of locking features 226 formed on second sections 224a, 224b of respective legs 220a, 220b of attachment portion 220 of shipping cap 200 are received within large openings 115 formed in outer cylindrical portion 112 of housing 110 of loading unit 100. Receipt of flanges 227 within large openings 115 secures shipping cap 200 to housing 110. As shown in FIG. 8, large openings 115 are configured to accommodate flanges 227 without flexion of flanges 227. In this manner, legs 220a, 220b of leg portions 220 are capable of being flexed away from outer cylindrical portion 112 of housing 110 to withdraw flanges 227 of locking features 226 from within large openings 115. As such, when shipping cap is in the first orientation on housing 110 of loading unit 100, shipping cap 200 is releasably secured to loading unit 100. In the first orientation, extensions 232 of shipping cap 200 engage shelf 140 of pusher member 130 of loading unit 100 to prevent advancement of pusher member 130.

Loading unit 100 is provided to a clinician with shipping cap 200 attached to the loading unit 100 in the first orientation. When shipping cap 200 is attached to loading unit 100 in the first orientation, loading unit 100 may be secured to elongate body 16 (FIG. 1) of actuation unit 12 (FIG. 1) in a conventional manner. As noted above, housing 110 of loading unit 100 may be connected to elongate body 16 of actuation unit 12 using a bayonet coupling or in any other suitable manner. The pusher member 130 is connected to drive member 18 (FIG. 5) of actuation unit 12 through receipt of tab 135 formed on a proximal end of arm 134 of pusher member 130 within a notched distal end 18a (FIG. 5) of drive member 18 (FIG. 5). Once loading unit 100 is secured to actuation unit 12 (FIG. 1), shipping cap 200 may be removed.

With continued reference to FIGS. 7 and 8, removal of shipping cap 200 from loading unit 100 is accomplished by flexing legs 220a, 220b of attachment portion 220 away from outer cylindrical portion 112 of housing 110 of loading unit 100, as indicated by arrows "A" in FIG. 7. As noted above, the configuration of large openings 115 in outer cylindrical portion 112 of housing 110 permits removal of locking feature 226 of legs 220a, 220b from within large openings 115 as legs 220a, 220b are flexed away from outer cylindrical portion 112. Tabs 229 formed on each of legs 220a, 220b of attachment portion 220 facilitate engagement, i.e., grasping, of legs 220a, 220b by the clinician. Once legs 220a, 220b are sufficiently flexed away from housing 110 such that locking features 226 are completely removed from within large openings 115, shipping cap 200 can be slid from about outer cylindrical portion 112 in a distal direction, as indicated by arrow "B", to effect separation of the shipping cap 200 form the loading unit 100. Once the shipping cap 200 is separated from the loading unit 100, the loading unit 100 to be used in a conventional manner.

Following a stapling procedure using the surgical stapling device 10 (FIG. 1), shipping cap 200 is reattached to loading unit 100 to prevent subsequent re-firing of loading unit 100 and to facilitate separation of the loading unit 100 from the elongate body 16 of the actuation unit 12. In particular, the legs 220a, 220b of shipping cap 200 are positioned on opposite sides of loading unit 100, as indicated by arrow "C" in FIG. 9, such that extensions 232 of shipping cap 200 are received within distal end 136 of pusher member 130 and locking features 226 of shipping cap 200 align with small openings 117 of outer cylindrical portion 112 of housing 110. Once the locking features 226 of shipping cap 200 are aligned with small openings 117 formed in outer cylindrical portion 112 of housing 110, legs 220a, 220b of attachment portion 220 of shipping cap 200 are pushed radially inward, as indicated by arrows "D" in FIG. 9 to force the projections 228 formed on flanges 227 into engagement with the outer cylindrical portion 112 of housing 110. Continued application of the radially inward force on legs 220a, 220b causes flanges 227 of locking features 226 to flex inward towards one another, thereby allowing flanges 227 to be received within small openings 117. As legs 220a, 220b are pushed radially inward and flanges 227 of locking features 226 are received within small openings 117 of outer cylindrical portion 112 of housing 110, free ends 227a of flanges 227 engage arms 134 of pusher member 130 of loading unit 130. Engagement of arms 134 of pusher member 130 by flanges 227 cause arms 134 to flex radially inward, as indicated by arrows "E" in FIG. 9, to facilitate separation of pusher member 130 of loading unit 100 from drive member 18 (FIG. 5) of actuation unit 12 (FIG. 1).

Figure 10:
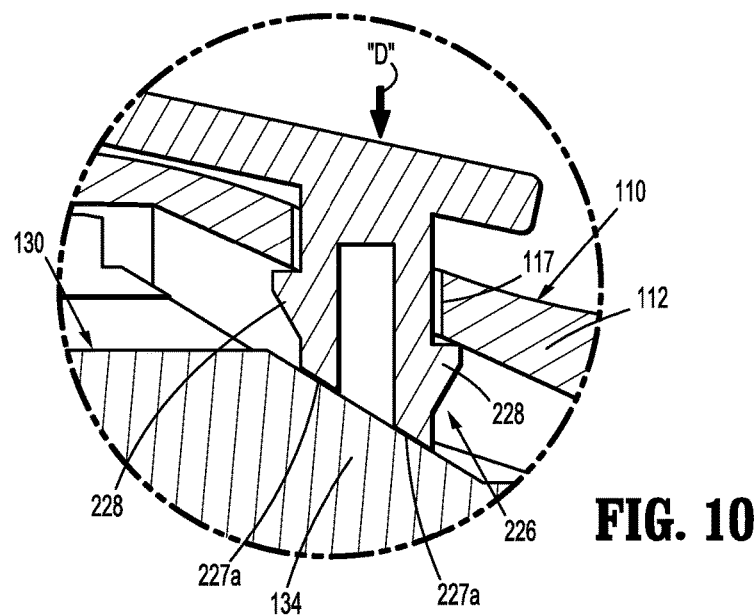
FIG. 10 is an enlarged view of the indicated area shown in FIG. 9.

With particular reference to FIG. 10, once locking features 226 of shipping cap 200 are fully received through small openings 117 in outer cylindrical portion 112 of housing 110, flanges 227 of locking features 226 return to an initial, non-flexed condition. In the initial condition, projections 228 extending from flanges 227 of locking features 226 engage an inner surface of outer cylindrical portion 112 of housing 110. Engagement of outer cylindrical portion 112 by projections 228 prevents removal of locking features 226 from within small openings 117, thereby securing shipping cap 200 to loading unit 100.

Once shipping cap 200 is reattached to loading unit 100 in the second orientation, loading unit 100 can be separated from elongate body 16 (FIG. 1) of actuation unit 12 (FIG. 1) in the conventional manner, e.g., rotating loading unit 100 in relation to elongate body 16. Additional loading units 100 can then be attached to actuation unit 12 and used in the manner described above.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A loading unit for a circular stapling apparatus comprising:
  a housing defining a pair of first openings and a pair of second openings, wherein the first openings are larger than the second openings;
  a pusher assembly operably received within the housing and being movable from a first position to a second position within the housing;
  a staple cartridge disposed on a distal end of the housing and including a plurality of staples; and
  a shipping member operably received on a distal end of the housing to prevent movement of the pusher assembly from the first to the second position, the shipping member being receivable on the housing in a first orientation and a second orientation, wherein in the first orientation the shipping member is removably secured to the housing and in the second orientation the shipping member is fixedly secured to the housing.

2. The loading unit of claim 1, wherein the shipping member includes,
  a base portion;
  a pair of legs extending from the base portion; and
  a locking feature disposed on a free end of each of the pair of legs, wherein the locking features are removably securable within the pair of first openings and fixedly securable within the pair of second opening.

3. The loading unit of claim 2, wherein each locking feature includes a pair of flanges.

4. The loading unit of claim 3, wherein each of the pair of flanges is configured to flex inwardly to facilitate entry of the flanges into one of the second openings.

5. The loading unit of claim 4, wherein each flange includes a projection extending radially outward therefrom.

6. The loading unit of claim 2, wherein each leg of the pair of legs includes a tab to facilitate operable engagement by a user.

7. The loading unit of claim 1, wherein the base portion of the shipping member includes an inner surface configured to be disposed adjacent the staple cartridge, the inner surface of the base portion being configured to maintain the plurality of staples within the staple cartridge.

8. The loading unit of claim 1, wherein the shipping member further includes a retaining portion extending proximally from the base portion, the retaining portion being configured to engage the pusher assembly.

9. The loading unit of claim 8, wherein the retaining portion includes at least one extension.

10. The loading unit of claim 9, wherein the at least one extension includes a pair of extensions.

11. A surgical stapling device comprising:
  a body portion;
  a loading unit removably secured to the body portion; and
  a shipping member operably received on a distal end of the loading unit, the shipping member being receivable on the loading unit in a first orientation and a second orientation, wherein in the second orientation the shipping member permits separation of the loading unit from the body portion.

12. The surgical stapling device of claim 1, wherein the loading unit includes a pusher assembly and the body portion includes a drive assembly, the pusher assembly being removably secured to the drive assembly.

13. The surgical stapling device of claim 12, wherein engagement of the shipping member with the pusher assembly disengages the pusher assembly from the drive assembly.

14. The surgical stapling device of claim 13, wherein the shipping member includes at least one retaining portion for engaging the pusher assembly.

15. The surgical stapling device of claim 14, wherein the loading unit includes a housing and the at least one retaining feature includes projection, the projection engaging the housing when the shipping member is in the second orientation to fixedly secure the shipping member to the housing.

16. A method of stapling tissue comprising:
  attaching a loading unit to a surgical stapling device, the loading unit including a shipping member secured thereto in a first orientation;

removing the shipping member from the loading unit;
performing a stapling procedure with the surgical stapling device and the loading unit; and
securing the shipping member to the loading unit in a second orientation.

17. The method of claim 16, further including separating the loading unit from the surgical stapling device subsequent to securing the shipping member to the loading unit in the second orientation.

18. The method of claim 16, wherein securing the shipping member to the loading unit includes engaging a retaining portion of the shipping member with a pusher assembly of the loading unit.

19. The method of claim 18, engaging the retaining portion of the shipping member with the pusher assembly includes disengaging the pusher assembly from a drive assembly of the surgical stapling device.

* * * * *